United States Patent
Gerlach et al.

(10) Patent No.: US 10,098,726 B2
(45) Date of Patent: Oct. 16, 2018

(54) EYE LENS WITH A SPECIFICALLY SHAPED TRANSITION REGION OF AN OPTICAL PART

(71) Applicant: Carl Zeiss Meditec AG, Jena (DE)

(72) Inventors: Mario Gerlach, Glienicke-Nordbahn (DE); Beate Boehme, Grosspuerschuetz (DE); Hans-Juergen Dobschal, Kleinromstedt (DE)

(73) Assignee: Carl Zeiss Meditec AG, Jena (DE)

( * ) Notice: Subject to any disclaimer, the term of this patent is extended or adjusted under 35 U.S.C. 154(b) by 220 days.

(21) Appl. No.: 15/045,129

(22) Filed: Feb. 16, 2016

(65) Prior Publication Data

US 2016/0157994 A1 Jun. 9, 2016

Related U.S. Application Data

(63) Continuation of application No. PCT/EP2014/066700, filed on Aug. 4, 2014.

(30) Foreign Application Priority Data

Aug. 13, 2013 (DE) ........................ 10 2013 216 014

(51) Int. Cl.
*A61F 2/16* (2006.01)
*G02C 7/06* (2006.01)
*G02C 7/02* (2006.01)

(52) U.S. Cl.
CPC .......... *A61F 2/1627* (2013.01); *A61F 2/1618* (2013.01); *A61F 2/164* (2015.04); *A61F 2002/1681* (2013.01); *A61F 2230/0063* (2013.01); *A61F 2230/0069* (2013.01); *G02C 7/028* (2013.01); *G02C 7/063* (2013.01)

(58) Field of Classification Search
CPC .................. A61F 2/1627; A61F 2/1618; A61F 2002/1681; A61F 2230/0069; A61F 2/164; G02C 7/028; G02C 7/063; G02C 2202/22

See application file for complete search history.

(56) References Cited

U.S. PATENT DOCUMENTS

| 6,533,416 B1 | 3/2003 | Fermigier et al. |
| 2014/0211313 A1 | 7/2014 | Dobschal |

OTHER PUBLICATIONS

International preliminary report on patentability dated Feb. 16, 2016 in international patent application PCT/EP2014/066700 on which the claim of priority is based.
International Search Report dated Oct. 29, 2014 in international patent application PCT/EP2014/066700 on which the claim of priority is based.

*Primary Examiner* — David H Willse
*Assistant Examiner* — Tiffany Shipmon
(74) *Attorney, Agent, or Firm* — Walter Ottesen, P.A.

(57) ABSTRACT

An eye lens includes an optical part, which defines a first optical surface. The first optical surface is configured as turn with a pitch extending circumferentially about a principal axis (A) of the eye lens. A transition region is formed between a beginning and an end of the turn, which with a beginning edge and an end edge merges into the turn. The beginning edge extends between the principal axis (A) and a first circumferential location and the end edge extends between the principal axis (A) and a second circumferential location. The beginning edge projected into a plane (H) perpendicular to the principal axis (A) has a non-linear course and/or the end edge projected into a plane (H) perpendicular to the principal axis (A) has a non-linear course.

27 Claims, 6 Drawing Sheets

EYE LENS WITH A SPECIFICALLY SHAPED TRANSITION REGION OF AN OPTICAL PART

CROSS REFERENCE TO RELATED APPLICATIONS

This application is a continuation application of international patent application PCT/EP2014/066700, filed Aug. 4, 2014, designating the United States and claiming priority from German application 10 2013 216 014.3, filed Aug. 13, 2013, and the entire content of both applications is incorporated herein by reference.

FIELD OF THE INVENTION

The invention relates to an eye lens, in particular an intraocular lens, comprising an optical part, which comprises a first optical surface.

BACKGROUND OF THE INVENTION

Eye lenses in the form of intraocular lenses have an optical part, to which commonly a haptic part connects. With the haptic part the intraocular lens is retained in the capsular bag of the eye. The optical part can be configured in manifold ways, in order to be able to correct the corresponding defects of vision in a human eye. In this connection the surfaces of the optical part can be configured to be spheric or aspheric. Also toric eye lenses are known.

Especially in the case of very complex surface shapes of the optical part the manufacturing of the eye lens is difficult and complex. The manufacturing tool needs to be positioned extremely precisely on the lens material, in order not to generate any undesired shapes, which then would impair the optical properties of the lens.

Since, however, there are limits to the manufacturing process with such tool with regard to the theoretically determined and calculated eye lens with respect to the generation of such an explicit optimum, this has to be taken into account. Accordingly in practice frequently problems occur in the case of very jagged or discrete steps on the surface of the optical part during manufacture. This is because here very large accelerations occur on the manufacturing tool, which may lead to corresponding problems in the material processing of the eye lens.

SUMMARY OF THE INVENTION

It is an object of the present invention to configure an eye lens in the optical part in such a way that at least one unchanging optical imaging property can be achieved, while enhancing manufacturability.

An eye lens according to the invention includes an optical part, which has at least one optical surface. This first optical surface viewed in the radial direction at least in portions is configured as turn with a pitch extending circumferentially around a principal axis of the eye lens. The principal axis is the optical principal axis of the eye lens. This first optical surface thus at least in portions is configured as spiral path extending circumferentially around the principal axis. By such a turn of the surface and the generated pitch thus in the direction of the principal axis a certain offset between a beginning and an end of the turn occurs. Between this beginning and the end of the turn a transition region of the optical surface is formed. This transition region is configured with a beginning edge and an end edge merging into the turn. The beginning edge extends between the principal axis and a first circumferential spot of the optical path and the end edge extends between the principal axis and the second circumferential spot. The beginning edge projected into a plane perpendicular to the principal axis has a non-linear progression, wherein additionally thereto or instead the beginning edge of the transition region projected into a plane perpendicular to the principal axis has a non-linear progression. An optical surface wound in such a specific way to start with comprises this transition region between its beginning and its end. It is an essential focus of the invention to optimize same with regard to the best possible optimum imaging properties of the first optical surface and best possible manufacturability. In this connection an abrupt complete stepped transition comprising a quasi vertical wall between the beginning and the end with regard to a theoretical representation of the eye lens is the optimum transition. As same cannot be formed in manufacture, it is an essential aspect of the invention to configure this transition region form-specifically in such a way that with regard to the optimum imaging property of the eye lens and at the same time precise manufacturability a maximum is achieved.

This is generated by the entirely deliberately cornerless configuration of the transition region with a cornerless merging into the beginning and the end of the turn. In a way that is to be particularly highlighted, this solution of the problem, however, is achieved by the very specific progression of the beginning edge and the end edge of the transition region. By such a specific configuration the transition region can be practically minimally dimensioned and the desired optical properties of the optical surface can be quasi maximized in comparison with the theoretical optimum and moreover also the manufacturing precision of the simulated lens be essentially improved. Since by this detailed specific dimensioning and form configuration of the transition region the manufacturing tool is not exposed to any undesired abrupt high accelerations, the configuration of the transition region can be effected by the tool in an extremely precise and accurate way. As now no undesired and abrupt accelerations occur anymore for the tool, also undesired material ablations or insufficiently ablated material in lens manufacturing can be avoided.

It can be envisaged that the entire optical surface is configured as wound structure, which comprises a complete turn or several turns around the principal axis. In this embodiment then the beginning edge extends directly starting from the principal axis up to the circumferential spot and thus over the entire length between these end points. The same in analogy then applies to the end edge.

However, it can also be envisaged that the optical surface besides a first portion, which comprises one turn or several turns, comprises a second portion, which comprises no wound structure. For instance here it can be envisaged that the second portion is a central centre portion, which comprises a spheric or aspheric surface, to which the first portion radially connects. The first portion can then for instance be a monofocal lens. In this embodiment then the beginning edge starting at the circumferential spot extends between the circumferential spot and up to the point, at which viewed in the radial direction the first portion ends. While the beginning edge is then also configured to extend between the principal axis and the circumferential spot, however, it does not extend completely up to the principal axis and thus ends spaced apart from the principal axis. The same is true for the end edge.

The pitch is the height of the turn in the direction of the principal axis between the beginning and the end.

Preferably it is envisaged that the beginning edge and/or the end edge is or are curved over the entire length. Such a configuration of at least one edge facilitates the above-named advantages once again. Thus, a very continuous and even shape configuration of an edge is given, whereby no abrupt steps and thus also no abrupt changes in acceleration and thus direction of the manufacturing tool are given. The very connection of a non-linear beginning edge and/or end edge in projection onto the principal plane with a cornerless progression of such an edge steadily curved into one direction essentially facilitates the above-named advantages.

Preferably it is envisaged that the beginning edge has a non-linear progression, which in comparison to a linear connection between the principal axis and the first circumferential spot viewed in the circumferential direction about the principal axis is configured to extend in the direction towards the end edge. Additionally or instead it may be envisaged that the end edge has a non-linear progression, which in comparison to a linear connection between the principal axis and the second circumferential spot viewed in the circumferential direction about the principal axis is configured to extend in the direction towards the beginning edge. Especially these curvature directions of the edges allow for keeping the configuration of the transition region as small as possible and thus for improving the optical imaging properties of the lens towards the theoretical optimum. At the same time the manufacturing precision, however, is also positively favoured.

Preferably it is envisaged that a surface of the transition region is shaped in such a way that at least at the beginning edge, in particular over its entire length, between the principal axis and the first circumferential spot a progression is configured, in which the gradient of the surface viewed in the circumferential direction in all radial places has the same progression of the gradient. The contour or the course of the contour of the surface is thus configured in such a way that at the beginning edge the mathematical functional gradient progression quasi is the same over the entire radial length of the beginning edge. Thus in every radial place of the beginning edge the corresponding gradient viewed in the azimuthal direction is configured with the same functional gradient progression and thus the same description function for the gradient. Thus the same gradient is configured everywhere in the places, which in particular means that the acceleration for the manufacturing tool in these places is constant, since the acceleration mathematically represents the derivation of the gradient. By this very specific shaping of the surface the minimization of the transition region and thus at the same time best possible optical manufacturable imaging property of the optical first surface is achieved. It is virtually a maximum of the parameter of a small transition region, a best possible imaging property, and exact manufacturability of the simulated transition region is achieved.

Preferably it is envisaged that a surface of the transition region is shaped in such a way that at least at the end edge, in particular over its entire length between the principal axis and the second circumferential spot a progression is configured, in which the gradient of the surface viewed in the circumferential direction in all radial places of the end edge has the same gradient progression. The above-named advantages here apply in analogy.

Preferably it is envisaged that a surface of the transition region viewed in the circumferential direction has a course of the contour, which at least in portions is configured to be non-linear. In particular this surface configuration is configured accordingly in all radial places between the principal axis and the circumference of the optical part. This means, if thus a section is drawn at a radial place in the optical part through the transition region, the course of the contour of the surface is configured to be non-linear over its entire length. On the one hand, thereby a particularly continuous and smooth transition towards the ends of the turn of the optical first surface can be facilitated, on the other hand, an improved geometry of the transition region with regard to the optical properties and the manufacturing possibilities can be achieved.

Preferably, it is envisaged that the course of the contour is at least in portions configured as a parabola. This shape configuration of the course of the contour is particularly advantageous, since it allows for a configuration of the transition region that can be dimensioned particularly minimally in the azimuthal extension. Such shape configuration thus allows for a very limited transition region with minimal surface area, whereby the optical imaging properties of the optical part can be particularly approximated with regard to the theoretical optimum. Rather, the manufacture of such course of the contour is very exactly possible.

It may also be envisaged that the course of the contour at least partly is described by a cubic function or at least partly represents a circular path section. These two alternative shape configurations for the course of the contour facilitate a clear enhancement in comparison with the known configurations with regard to the enhancement of the optical imaging properties and the simultaneous enhancement of manufacturability.

It may also be envisaged that the course of the contour of the surface of the transition region between the beginning edge and the end edge is symmetrical to a symmetrical surface situated in the circumferential direction about the principal axis at the same angle distance from each of the beginning edge and the end edge, in particular the symmetry plane, which comprises the principal axis and the symmetry point. Preferably, this symmetry plane thus forms the point of departure, from which then the azimuthal functional shape description of the optical surface and thus the description in the circumferential direction is given. This symmetry plane thus is orientated perpendicular to the principal plane of the eye lens and thus to the principal plane of the optical part, on which then the principal axis is positioned perpendicularly.

By such symmetrical configuration of the course of the contour, which is configured to be correspondingly symmetrical in the radial direction from the principal axis up to the circumferential spot or the circumference in all places, the advantages with respect to improved optical imaging behaviour and improved manufacturability can be facilitated.

Preferably, it is envisaged that the functional gradient progression and thus the mathematical formula description of the gradient between the beginning edge and the symmetry plane is the same in all radial places. This concerns that portion of the optical surface, which is configured with at least one turn.

In particular it is envisaged that a surface area of the transition region projected into the principal plane, which is perpendicular to the principal axis, and bounded by the projected beginning edge and the projected end edge, is smaller than a surface in this principal plane that is bounded by two linear surface edges, one of which extends from the principal axis through the first circumferential spot and the further one extends from the principal axis through the second circumferential spot.

Preferably it is envisaged that an end edge, which viewed in the direction of the principal axis is situated closer to the principal plane, has a non-linear progression.

In particular it is envisaged that the end edge projected into the principal plane is curved towards the projected beginning edge. In particular it is envisaged in this connection that starting from the second circumferential spot the end edge towards the projected beginning edge is steadily curved. Preferably the same is true in analogy for the projected beginning edge with reference to the end edge.

The surface of the transition region is configured to be entirely devoid of steps.

It is envisaged in particular that the surface of the transition region is curved and thus shaped in such a way, and the end edge and the beginning edge are configured in such a way that the gradient in all points of the beginning edge over the length of the beginning edge viewed in the radial direction varies by a maximum of 10%, in particular is the same. The same applies in analogy in an advantageous way to the end edge.

Preferably it is envisaged that an asphericity of the first optical surface viewed extending around the principal axis varies. In particular it is envisaged here that it continuously varies, in particular continuously enlarges.

In an advantageous way it is envisaged that at least one surface of the optical part is configured in such a way that the refractive power of the optical part in the circumferential direction about the principal axis in the case of a rotation changes by a value of between 1 diopter and 5 diopters, in particular between 1 diopter and 4 diopters, and/or preferably changes continuously. In the case of a single complete turn and thus a single circulation thus in particular such diopter change is effected.

Preferably in this connection it is started from a beginning diopter value, which lies at between 19 and 22 diopters, preferably at 20 diopters. In the case of a single rotation then an above-named advantageous change of diopter is performed so that this then increases by the corresponding indicated advantageous interval.

Preferably it is envisaged that the power of the optical part of the eye lens changes outside the transition region linearly as function of the angle in the circumferential direction about the principal axis. Such configuration is particularly advantageous with regard to the formation of a depth of focus lens with a correspondingly extended focal range, in which then the power distribution occurs particularly uniform and harmonious and thus the optical imaging behaviour is particularly facilitated via a corresponding diopter value.

Preferably it is envisaged that the transition region, in particular measured between the two circumferential spots, in the circumferential direction has an angle width <7°, in particular between 5° and 6.5°. Such small dimensioning of a transition region is facilitated by the shape configurations of the surface as well as the beginning edge and the end edge named in the above.

Preferably it is envisaged that the first optical surface of the optical part has a shape, which can be described by a function depending on a sum of sine functions. In particular thus the progression of the turn and thus the spiral path is not linear, but dependent on cosine functions. The above-named advantages with regard to the optical imaging behaviour, precisely with regard to the advantageously named diopter changes, are thereby particularly suitable.

Preferably, it is envisaged that a rear second optical surface of the optical part is configured to be symmetrical to the first optical surface with regard to the principal plane extending perpendicularly to the principal axis. In such a two-sided configuration in each case with a turn extending once around the circumference and with a corresponding pitch and a corresponding transition region it is possible that the diopter value changes, as they have already been mentioned in the above in an exemplary way, are distributed on both sides and thus on both surfaces. This means that on each surface no longer the full desired diopter value change must be reached in a single complete circulation, but in this regard only half the value of the desired change in diopter value has to be achieved. Thus on both sides in each case for instance a diopter change from 10.5 to 12 diopters can be envisaged in the case of a turn so that in total a change of 21 to 24 occurs.

Advantageously, the surface configuration of the optical part is such that the eye lens has a refractive structure.

In particular the turn is configured to extend only once around the axis and from the principal axis up to the circumference without multiple wave and valley shape.

Preferably it is envisaged that at least one haptic part is arranged and configured to adjoin to the optical part, and a transition zone has a surface, the contour of which at least in portions has a circular arc shape or a parabola shape. In this connection in particular the radius of this circular arc is azimuthally changeable. In particular it is envisaged that the transition between the contour of the optical part and the contour of the haptic part and thus the configuration of the transition zone is configured without a straight-line section.

It is particularly advantageous if the eye lens is configured as depth of focus lens. In particular it is an intraocular lens. In a particularly advantageous way it is envisaged that the angle ranges in the circumferential direction about the principal axis and thus the azimuthal angle ranges with regard to a change of the power and thus the diopter values are divided in such a way that in a first angle range, in particular starting at the beginning of the turn, between 115° and 119°, in particular 118° a diopter value change of between 0.5 and 1.5, in particular of 1, occurs, in an adjacent further angle range of once again between 115° and 119°, in particular 118°, a further diopter value change of between 0.5 and 1.5, in particular of 1, occurs, and in particular in a third angle range of equally preferably between 115° and 119°, in particular 118°, a further diopter value change of between 0.5 and 1.5, in particular of 1, occurs, so that in a continuous angle range of preferably 354° a diopter value change of 3 diopters is achieved.

It may also be envisaged that a diopter value change greater than 3 occurs, for instance by a value of up to 3.7, so that for instance also a change by 3.3 can occur.

Preferably in this angle range of the turn outside the transition region the power changes linearly as function of the azimuth angle.

In an advantageous way it is envisaged that for an increased intensity in the distance and the vicinity of the eye lens a diopter value change between 0.3 and 0.7, in particular of 0.5 is configured in a first angle range, in particular starting at the beginning of the turn, between 148° to 154°, in particular of 152°. In an adjacent second angle range of preferably equally between 148° to 154°, in particular of 152° then a diopter value change between 1.8 and 2.2, in particular of further 2 diopters, is envisaged, wherein here it is continued at the diopter value, which is achieved at the end of the first angle range.

In a third angle range, which is adjacent to the second angle range and preferably extends between 46° and 60°, in particular 50°, then a further diopter value change of between 0.3 and 0.7, in particular by 0.5 diopters, is formed, wherein here, too, preferably it is started from a diopter value that has been achieved at the end of the second angle range.

Preferably here, too, the transition region with an azimuthal width of 6° is configured, which in particular is measured at the external radial end and thus between the two circumferential spots.

Preferably it is envisaged that z values and thus the values of the surface of the eye lens in the direction of the principal axis as function of the angle $\varphi$, which is measured in the circumferential direction about the principal axis and represents the azimuth angle, generally can be described as the sum of sine functions, as shown by the following formula 1:

$$z(r,\varphi) = z_{max}(r) * z(\varphi) = z_{max}(r) * \Sigma a_n \sin(n\varphi) \tag{1}$$

Herein (r) refers to the radius, $\varphi$ to the azimuth angle (with $-\pi \leq \varphi \geq \pi$) and $a_n$ to the coefficients.

In the simplest of cases the pitch can here be $z_{max}(r) = C*r^2$, however, it can also be aspherical. C in this connection describes a constant and determines the maximum diopter value change of a complete circulation or a turn, and the function $z_w(r, \varphi)$ is between −1 and +1.

If preferably the angle $\varphi = 0$ lies in the centre of the transition region and thus in the symmetry plane, correspondingly advantageous calculations result.

Preferably this turn or this spiral shape of the surface is applied to a basic lens, which can be described by the function $z_0(r)$. In this connection an overall description of the surface is rendered, which can be described by the following formula 2:

$$z_{overall}(r,\varphi) = z_0(r) + z(r,\varphi) \tag{2}$$

In a particularly advantageous way it is envisaged that at least one optical surface of the optical part is configured and shaped in such a way that also an astigmatism is corrected as visual defect of the eye. Preferably it is envisaged in this connection that the surface is described by a further summand in the equation indicated in formula 2, wherein the summand can be described by $a_2*r^2*\sin(2*\varphi)$. The optical surface is configured to be at least in portions saddle-like or toric for the correction of the astigmatism.

Preferably it is envisaged that the saddle surface, which is rendered by the above-named summand for the astigmatism correction, and the surface with the turn are orientated in such a way relative to each other and are made to overlap to form an overall surface shape in such a way that a top saddle point, which is the highest point at the edge of the surface shape, coincides azimuthally in the circumferential direction with the flattest curvature—equal to the maximum in the azimuthal progression—of the turn in the radial direction.

In particular a rotational angle in the circumferential direction around the axis between the saddle surface and the surface with the turn is configured in such a way that the maximum of the sine function of the summand, which describes the saddle surface, lies at the place of the flattest radius of the surface with the turn and the minimum of the sine function in the direction of the steepest radius of the surface with the turn or the zero-crossing of the sine function lies in the centre of the transition region, and the sine function decreases, when the spiral surface in the transition region equally decreases.

By a further summand $b_2*\cos(2*\varphi)$ the orientation of the astigmatism in comparison to the transition and thus the transition zone can be controlled randomly. It is advantageous that the turn or the spiral shape of the surface rotates in such a way in the eye that the second summand is omitted, and instead the coefficient $a_2$ is selected correspondingly.

As already mentioned, it is advantageous to describe the course of the contour of the surface of the transition range at least in portions by a parabola as basic shape. Thereby it can be achieved that the velocity and the acceleration of the manufacturing tool and thus the cutter relations, which are derivable therefrom, are rendered.

To the predetermined parabola then the desired azimuthal turn and thus the spiral function of the optical surface is steadily adjoined, wherein here in the simplest of cases a straight line can be provided.

By these configurations the transition region with the named function progressions is shaped at as small as possible absolute values of the acceleration so that the angle range can be kept small.

However, also similar curve progressions could be envisaged, wherein for instance between the two parabolae of a course of the contour of the transition region again a linear function is inserted. Further, the acceleration can also gradually increase to the maximum values.

Alternatively a linear spiral-shaped configuration of the optical surface with a cubic function progression in the transition region is possible.

In order to generally in a particularly advantageous way keep the acceleration and thus the second derivation of the function describing the surface and on the other hand the transition region as small as possible, the function $z(r,\varphi)$ is to be configured to depend in such a way on the radius that the acceleration of the manufacture machine for manufacturing the lens remains independent of the radius.

In particular this is also achieved by a reversal point of the parabolae, which is described by the subsequent parameter (d), being indicated in the following and set in dependency on the radius:

In this connection (e), which refers to the z value of the reverse point, is equated with the function $z_{max}$:

$$e = e(r) = z_{max}(r) = C(r/r_0)^2. \tag{3}$$

Then a fixed maximum acceleration (a) for all radii is predetermined. In the simplest of cases of the above-indicated radial function then reverse points are obtained, which in the vicinity of the optical principal axis have a smaller angle distance, which is rendered for $$d = d(r) = \sqrt{\frac{e(r)}{a}} = r*\sqrt{\frac{C}{a*r_0^2}} \tag{4}$$

In the case of smaller radii and thus towards the optical principal axis in this connection the angle distance of the reverse points decreases.

The surface of the transition region thus has the function description or the form:

$$z(r, \varphi) = z_{max(r)} * z(r, \varphi) = C\left(\frac{r}{r_0}\right)^2 * \left\{ C\left(\frac{r}{r_0}\right)^2 - a\left[\frac{r}{r_0} * \sqrt{\left\{\frac{C}{a}\right\}} - \varphi\right]^2 \right\} \tag{5}$$

The function $z(r,\varphi)$ is here no longer described as product of a function of the radius with a function of angle, but the azimuthal function additionally depends in particular on the angle.

In an advantageous embodiment it is envisaged that the curvature radius and asphericity on the front and the reverse side and thus the first optical surface or the second optical surface of the optical part of the eye lens varies linearly with the azimuth angle between the value of a basic power, which for instance can be 21 diopters, and an overall power. It may also be envisaged that only the front or the rear side is varied, wherein the refractive power difference of the starting lens then is selected to be double the value. Decisive is always that the desired refractive power change value is achieved at one circulation.

In particular it is envisaged that the first optical surface is configured in such a way that only a single turn of a spiral path is formed, wherein thus also the spiral path in the radial direction is formed as refractive optics.

An advantageous course of the z function is characterized in that the second derivation does not exceed a maximum value and the machine tool for cutting or manufacturing the eye lens requires only minor accelarations in the z direction.

Preferably this is achieved by the following azimuthal course of function of the optical surface.

$$z(\varphi) = \begin{cases} m_1\varphi & 0 \le \varphi \le x_1, m_1 \rangle 0 \\ m_2\varphi - m_2 & x_2 \le \varphi \le 1, m_2 \langle 0 \\ -a*(\varphi - d)^2 + e & x_1 \le \varphi \le x_2, a \langle 0 \end{cases} \quad (6)$$

for $0<\varphi<1$: further one has: $z(\varphi)=-z(-\varphi)$ for $-1\le\varphi\le0$ Preferably here the parameters (d) and (e) as in the equations 3 and 4 are indicated, depending on the radius.

Here the transition region is characterized by two parabolae with inverted sign, which adjoin to each other steadily or are connected by a straight line. To this function the summand $a_2*\sin(2*\varphi)$ can be added for the astigmatism.

The function $z(\varphi)$ increases starting at a mean value $z(\varphi=0)=0$ linearly with the increase $m_1$, then extends on a parabola and decreases with the increase $m_2$ back to the mean value.

In a particularly preferred configuration, the straight line portion with the increase $m_1$ connecting the parabolae can be omitted so that the transition between the two parabolae nonetheless occurs at x1=0, and a particularly small transition region with regard to its azimuthal extension is rendered. For all possible courses of function, for instance parabolic function, cubic function, or circular path section function, the respective parameters of the variables can be selected in dependency on the radius on the lens so that the transition region in particular towards the principal axis becomes very small.

In particular it is also envisaged that the surface configuration of the optical surface can also be correspondingly adapted and reduced for small pupils (r<1).

BRIEF DESCRIPTION OF THE DRAWINGS

The invention will now be described with reference to the drawings wherein.

DESCRIPTION OF THE PREFERRED
EMBODIMENTS OF THE INVENTION

In the figures, the same element or elements having the same function are provided with the same reference characters.

Figure 1A:
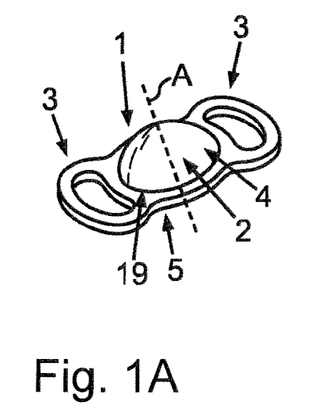
FIG. 1A is a perspective view of a first embodiment of an eye lens according to the invention.

In FIG. 1A, a perspective view of a first embodiment of an eye lens 1 is shown, which is an intraocular lens. The eye lens 1 includes an optical part 2 and adjoining thereto a haptics 3. The eye lens 1 is foldable and insertable via small incisions into the eye.

The optical part 2 defines an optical principal axis A, the direction of which is also the z coordinate. The optical part 2 moreover has a first optical surface 4 and a second optical surface 5 formed on the opposite side.

Figure 1B:
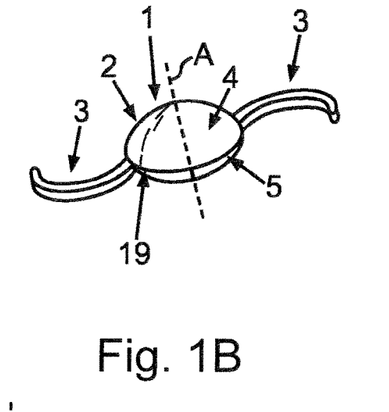
FIG. 1B is a perspective view of a further embodiment of an eye lens according to the invention.

In FIG. 1B in a perspective view, a further embodiment of an eye lens 1 configured as intraocular lens is shown. It differs from the embodiment in FIG. 1A by the different haptics 3.

Figure 2:
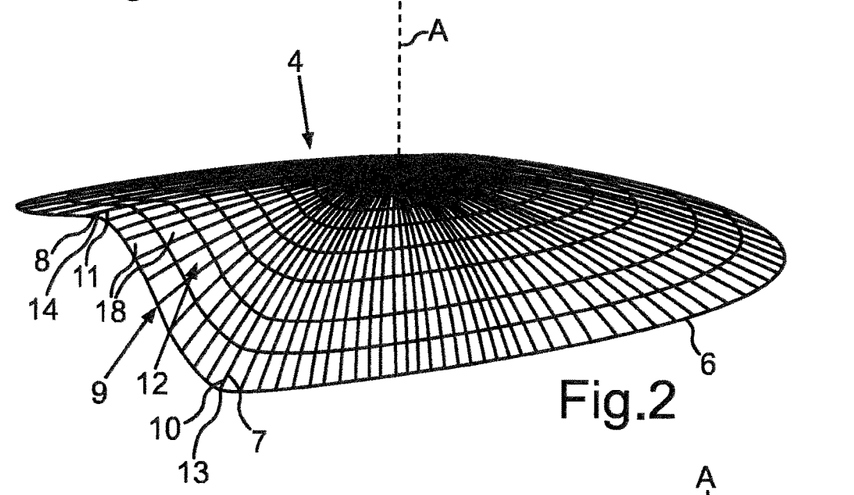
FIG. 2 is a perspective view of an embodiment of an optical surface of an optical part of an embodiment of an eye lens according to the invention.

In FIG. 2 in an enlarged view, an embodiment of the first optical surface 4 is shown. It is configured as curved spiral path shaped turn extending around the optical principal axis A. A single circumferential turn is configured, which extends in the radial direction and thus perpendicularly to the axis A from the axis A up to a circumference 6. The circumference 6 thus also preferably represents the outer end of the optical part 2.

The first optical surface 4 with regard to its spiral path thus is configured with a pitch, wherein the turn has a beginning 7 and an end 8.

Moreover, the first optical surface 4 has a transition region 9, which extends between the beginning 7 and the end 8. The transition region 9 is equally configured in the radial direction between the axis A and the circumference 6. In the circumferential direction about the axis A and thus in azimuthal orientation the transition region 9 includes a beginning edge 10 and an end edge 11. The transition region 9 in this connection with its beginning edge 10 merges directly into the beginning 7, wherein also the end edge 11 directly merges into the end 8.

A surface 12 of the transition region 9 is configured to be smooth and also the merging of the beginning edge 10 into the beginning 7 is configured to be smooth. Equally, the merging of the end edge 11 into the end 8 is configured to be smooth.

The beginning edge 10 here, too, extends from the principal axis A up to the first circumferential spot 13. The end edge 11 equally extends from the principal axis A to a second circumferential spot 14.

The transition region 9 with its beginning edge 10 and its end edge 11 is configured in such a way that in a projection of the beginning edge 10 and/or the end edge 11 into a plane, in particular the principal plane H (FIG. 10), perpendicular to the principal axis A same has/have a non-linear progression.

In particular the beginning edge 10 and/or the end edge 11 are configured to be curved over their entire radial length.

Figures 4, 5:
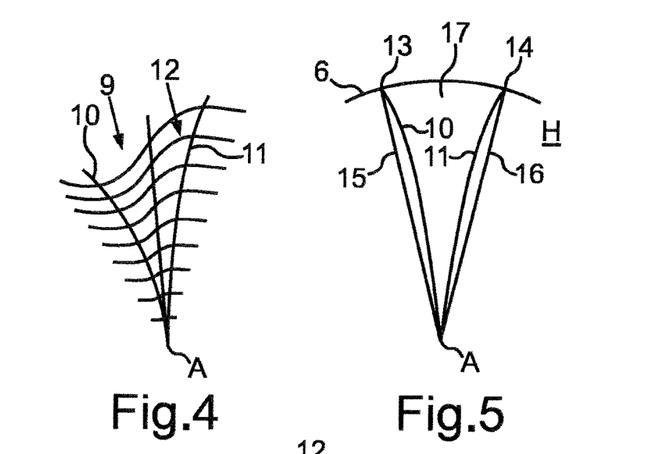
FIG. 4 is a different view of the transition region of an embodiment of an eye lens according to the invention.
FIG. 5 is a projection view of the transition region into a principal plane of the eye lens.

As can be seen in the projection view in FIG. 5 that is still to be explained, the beginning edge 10 and the end edge 11 are very specifically configured and curved.

The beginning edge 10 has a non-linear progression, which is configured to extend in comparison to a linear connection between the principal axis A and the first circumferential spot 13 viewed in the circumferential direction around the principal axis A in the direction towards the end edge 11. The beginning edge 10 in the projection plane H shown in FIG. 5 thus in particular over its entire length lies closer to the end edge 11 than a linear connection 15 between the axis A and the first circumferential spot 13.

Moreover, also the end edge 11 is configured to extend in a non-linear way and extends between axis A and the second circumferential spot 14 in the projection plane H shown in FIG. 5 in particular over its entire length closer to the beginning edge 10 than a straight connection 16 between the axis A and the second circumferential spot 14.

In the projection plane H shown in FIG. 5 and situated in the figure plane thus by the very specific arrangements and curvatures as well as configurations of the beginning edge 10 and/or the end edge 11 a surface area 17 of the transition region 9 is generated in the projection plane H, which is smaller than a surface area between the linear connections 15 and 16.

According to the representation in FIG. 2 it can be seen that the surface 12 of the transition region 9 is shaped in such a way that at least at the beginning edge 10, in particular over its entire radial length between the principal axis A and the first circumferential spot 13 a progression is formed, in which the gradient of the surface 12 in all radial places of the beginning edge 10 has the same functional and thus mathematically describable gradient progression. They thus have quasi the same increase, which according to FIG. 7 is linear, so that the acceleration according to FIG. 8, which is the derivation of FIG. 7, is constant in the region.

The embodiment according to FIG. 2 to FIG. 5 is such that the beginning edge 10 extends over the entire length between the principal axis A and the circumferential spot 13 and thus quasi merges into these end points. The same is true for the end edge 11. However, it could also be envisaged that the surface 4 is not configured over the entire region with a wound structure, but for instance in the center a region of a structure that is not wound is configured, for instance a monofocal lens, to which radially then a further region is adjacent, which has a wound structure. In this embodiment then the beginning edge 10 and the end edge 11 extend between the principal axis A and the circumferential spots, however do not merge into the principal axis but end radially spaced apart therefrom, in particular at the boundary between the two named regions.

Figure 6:
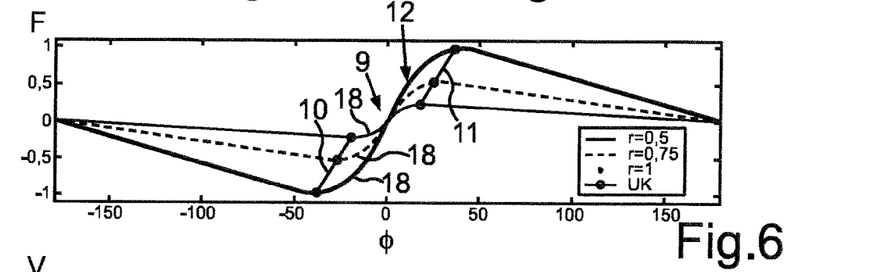
FIG. 6 is a diagram, in which the surface progression is shown in dependency on the azimuthal angle for various radii in the transition region.
Figure 7:
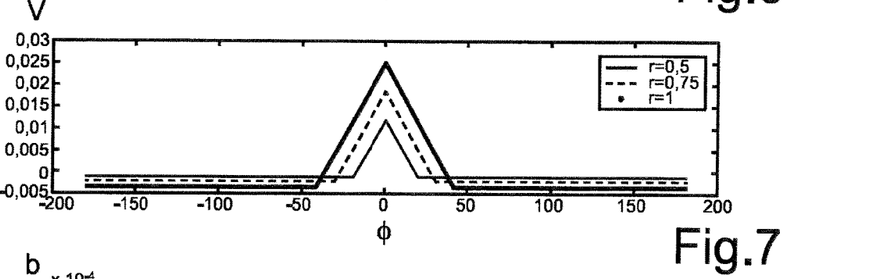
FIG. 7 is a diagram, in which the derivation of the mathematical function showing the surface shape in FIG. 6 is shown in dependency on the azimuth angle.
Figure 8:
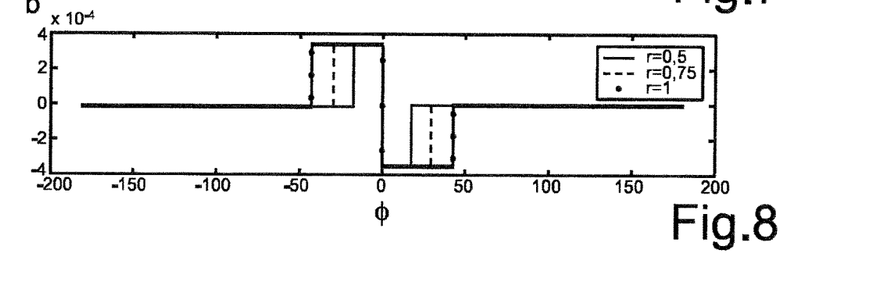
FIG. 8 is a diagram in which the acceleration and thus the second derivation of the mathematical function showing the surface shape in FIG. 6 is shown in dependency on the azimuth angle.

This is also shown by the represented diagrams in FIGS. 6 to 8. Here in FIG. 6 sectional views are shown in different radial places at the transition region 9, wherein the diagram in FIG. 6 shows the surface progression in dependency on the azimuthal angle φ. In the views according to FIGS. 6 to 8 a shape configuration of the transition region is shown, which is configured inverse to the representation in FIG. 2 and FIG. 3. This, however, is identical with regard to the realization and the functionality then actually achieved with it and both results and representations are identical with regard to their effect on the eye lens 1.

In particular it is also envisaged that the surface 12 of the transition region 9 is shaped in such a way that at least at the end edge 11, in particular over the entire radial length between the principal axis A and the second circumferential spot 14 a progression is configured, in which the gradient of the surface 12 viewed in the circumferential direction has the same functional gradient progression in all radial places of the end edge 11.

Figure 3:
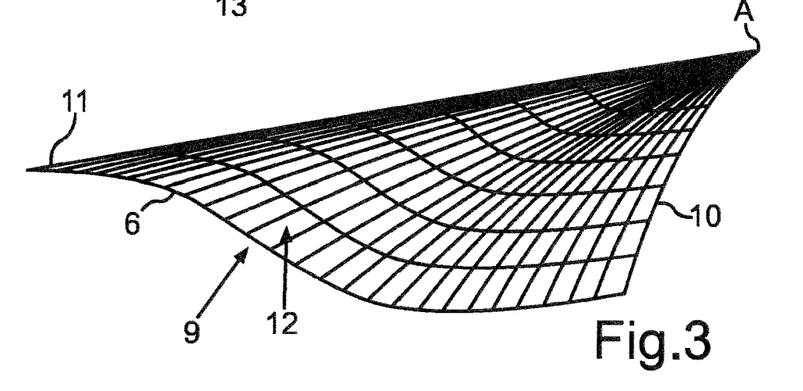
FIG. 3 is an enlarged section of the view according to FIG. 2.

As the views in FIG. 2 and FIG. 3 as well as in FIG. 6 to FIG. 8 illustrate, the surface 12 of the transition region 9 is configured in all radial places between the principal axis A and the circumference 6 of the optical part 2 with a course of the contour 18 viewed in the circumferential direction, which at least in portions is configured to be non-linear. The course of the contour of the surface 12 in this connection indicates that line or curve, which appears through the surface 12 in the case of a section through the transition region 9 at a specific radial place.

It is particularly preferred that this course of the contour 18, which for the sake of clarity in FIG. 2 is only symbolically drawn in at some places, is configured as parabola progression. Such progression is also explained in the diagrams according to FIG. 6 to FIG. 8.

In an advantageous embodiment it can be discerned that this course of the contour 18 between the beginning edge 10 and the end edge 11 is symmetrical to a symmetry point, which is situated in the circumferential direction around the principal axis A in each case at the same angle distance from the beginning edge 10 and the end edge 11 and which is situated in a symmetry plane that comprises the principal axis A and is orientated perpendicularly to the principal plane H.

In particular the functional gradient progression between the beginning edge 10 and the symmetry point is the same in all radial places. In a further advantageous configuration, it is envisaged that it varies over the entire length between an axis A and the circumference 6 maximally by 10%.

Preferably it is envisaged that z values and thus the values of the surface of the eye lens in the direction of the principal axis A as a function of the angle φ, which is measured in the circumferential direction about the principal axis A and represents the azimuth angle, are generally describable as a sum of sine functions, as is shown by the following formula 1:

$$z(r,\varphi)=z_{max}(r)*z(\varphi)=z_{max}(r)*\Sigma a_n \sin(n\varphi) \qquad (1)$$

With regard to the further determination reference is made to the explanations given as to afore-stated formulas 2 to 4.

In FIG. 3 an enlarged view of the transition region 9 of the first optical surface 4 according to FIG. 2 is shown.

In FIG. 4 moreover a perspective top view with simplified representation of the transition region 9 with the curved beginning edge 10 and end edge 11 is shown.

In the representations according to FIG. 7 and FIG. 8 the mathematically functional representations of the derivation as well as the second derivation of the surface function, as it is represented in FIG. 6 of the transition region 9, is drawn in. The mentioned same functional gradient progressions of the symmetrical configuration are shown in FIG. 7. Moreover, the constant second derivations, as they are given in all radial places between the beginning edge 10 and the symmetry plane, on the one hand, and the symmetry plane and the end edge 11, on the other hand, are shown. From FIG. 8 it can be seen that the acceleration does not go beyond a maximum value a, and in the overall transition region 9 between the beginning edge 10 and the end edge 11 remains the same.

In an exemplary way in the diagrams according to FIG. 6 to FIG. 8 in each case curve lines are shown for the radial places on the circumference 6 (r=1) and then shown for r=0.75 and r=0.5.

The surface 4 moreover in a first embodiment can be configured in such a way that starting from the beginning 7 a diopter value change of preferably three diopters is achieved. This is facilitated in particular in an angle interval range of 354°, wherein therein this diopter value continuously changes. Preferably the transition region 9 has an angle width of 6°, wherein here this angle width is preferably measured at the circumference 6.

In particular it is envisaged that for instance the power amounts to 21 diopters at the beginning 7 and 24 diopters at the end 8.

Thus, a change in the power outside the transition region 9 is given in such a way that it linearly changes as function of the angle in the circumferential direction about the principal axis A.

Figure 9:
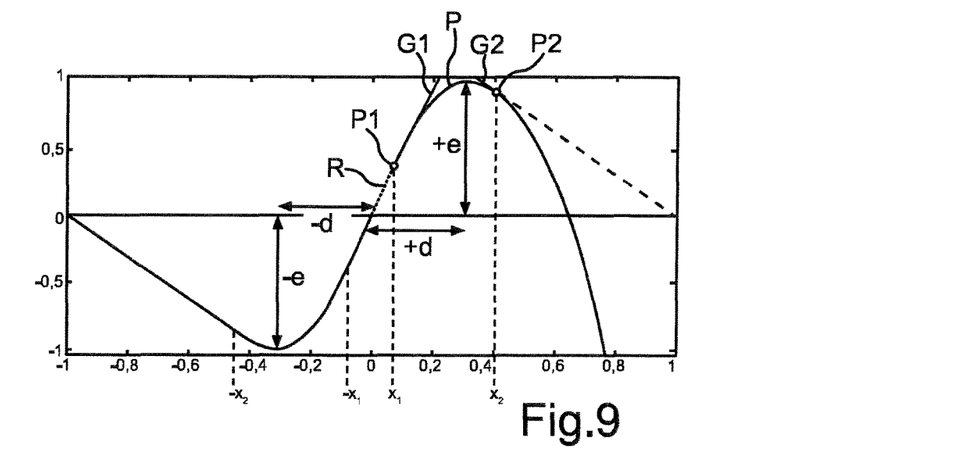
FIG. 9 is a diagram, in which in the embodiment an azimuthal function description of the surface of the transition region is shown.

In the diagram in FIG. 9 the functional progression and thus the mathematically descriptive function of the contour 18 of the surface 12 is shown in an exemplary way according to equation (6). In contrast to a direct joining of two parabolae, here between the parabolae a linear configuration and thus a corresponding course of the contour is imaged. In each case only the sections and places in the top region and thus above the horizontal axis are marked. In this connection R refers to the linear progression section of the straight line G1 with the increase m1, P1 the transition spot of the straight line G1 into the parabola (P, P2) the transition of the parabola into a straight line G2 with the increase m2. The transition region 9, however, is formed only up to the point P2 so that the remaining parabola representation is shown only for mathematical description. The surface as from the point P2 follows the straight line G2. The same applies in analogy to the curve progression below the horizontal axis, which derives from the symmetry about the point φ=0.

Figure 10:
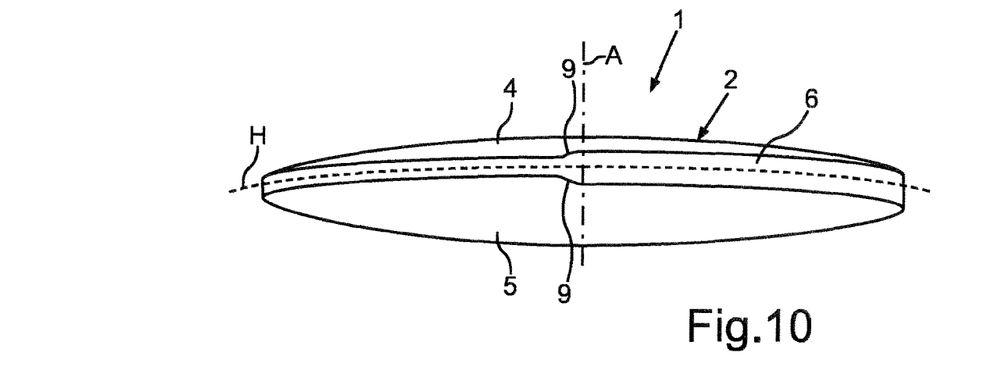
FIG. 10 is a perspective view of a further embodiment of an eye lens according to the invention, in which the optical part is shown with a partial view at a first and a second surface and the symmetrical surface configuration can be discerned.

In FIG. 10 in a perspective view a further embodiment of an eye lens 1 is shown. In contrast to the hitherto explanation this is configured in such a way that both the first optical surface 4 as well as the second optical surface 5 are configured with a single spiral path shaped turn and then a corresponding transition range 9 is configured at the pitch. Moreover it is envisaged that the surfaces 4 and 5 are configured to be symmetrical to the principal plane H, which is perpendicular to axis A. In such an embodiment thus the spiral path of the surface 4, as it was envisaged in an eye lens 1 configured to be merely on one side correspondingly structured, not to be configured with a diopter value change of three on one side, but with half of it. In addition the two symmetrically configured and structured surfaces 4 and 5 then again in total a diopter value change of preferably three in the case of a rotation about the axis A is rendered.

Moreover, it is envisaged that a transition zone 19 (FIGS. 1A and 1B) between the optical part 2 and the haptics 3 is configured with a surface, the contour of which in the radial direction is at least in portions a circular arc shape or a parabola shape. In particular this transition or this transition zone 19 between the contour of the optical part 2 and the contour of the haptic part 3 is configured without a linear course of the contour and thus with a corresponding section.

Figure 11:
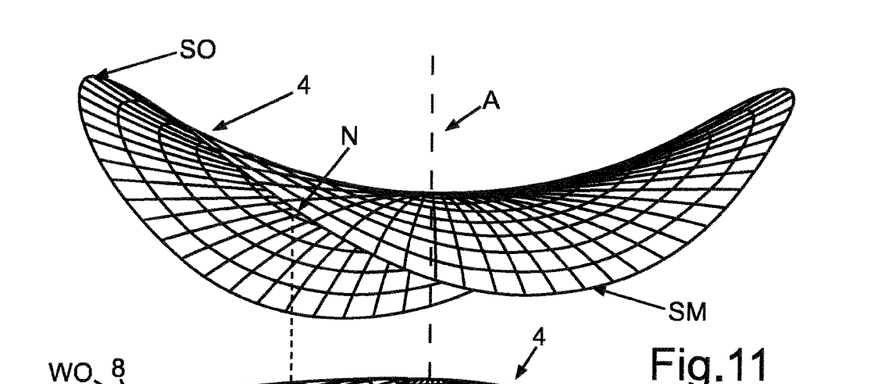
FIG. 11 is a perspective view of a surface, which shows the astigmatic summand portion in the function describing the overall surface.

In FIG. 11, a perspective representation of the surface is shown, which is generated by the summand $a_2*r^2*\sin(2*\varphi)$ for the astigmatism. The surface is configured as saddle surface so that on the lens surface a toric shape is rendered.

Figures 12, 13:
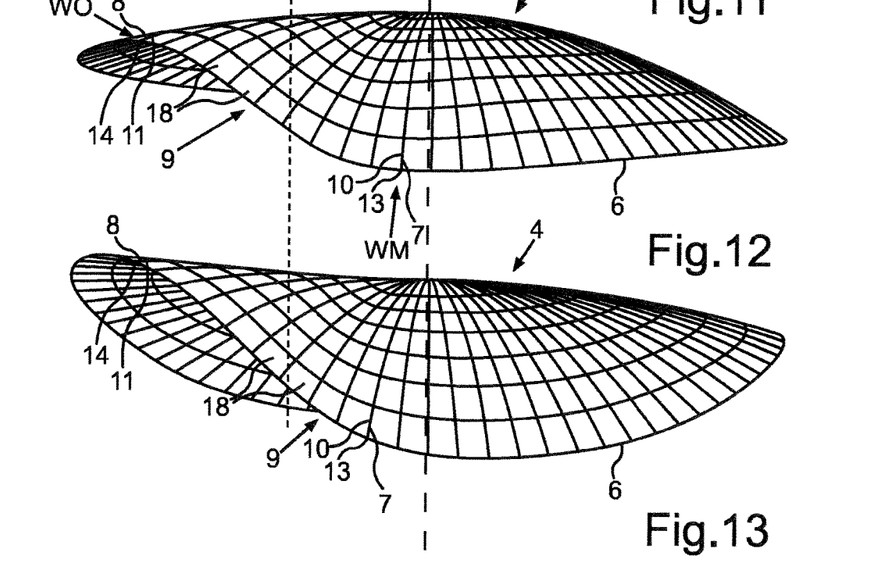
FIG. 12 is the view according to FIG. 2 in slightly rotated perspective in comparison with FIG. 2.
FIG. 13 is a perspective view of an embodiment of an optical surface of an optical part of an embodiment of an eye lens according to the invention, which is configured according to FIG. 12 and additionally the surface is configured in such a way that the lens serves for correction of an astigmatism.

In FIG. 12, a representation of the surface 4 according to FIG. 2 is shown, wherein in comparison with FIG. 2 a slightly rotated view is shown.

In FIG. 13, an embodiment of a lens configured for correction of an astigmatism with represented surface 4 of the optical part is shown. Therein the surface 4 in FIG. 12 is shown in a comparable position to FIG. 11 so that the difference from the surface shape can be recognized, between the lens with and without correction effect of an astigmatism.

In FIG. 13, the overlapping of the surfaces according to FIGS. 11 and 12 is shown. In this connection in the embodiment it is envisaged that for the surface according to FIG. 13 starting from the surface of FIG. 12 an additional saddle surface according to FIG. 11 is added so that an actual overall surface in FIG. 13 forms.

In particular in the embodiment it is envisaged that the saddle surface, which is rendered by the above-named summand for the astigmatism correction, and the surface with the turn in the circumferential direction about the principal axis A are orientated in such a way relative to each other and are overlapped to form a final overall surface shape formed on the lens that a top saddle point SO in FIG. 11 coincides with the flattest curvature WO in FIG. 12 of the turn.

In particular a rotation angle is configured in such a way in the circumferential direction about the axis A between the saddle surface and the surface with the turn that the maximum (saddle point SO) of the sine function of the summand describing the saddle surface lies at the place of the flatter radius (flattest curvature WO) of the surface with the turn and the minimum SM of the sine function in the direction of the steeper radius WM of the surface with the turn or the zero-crossing N of the sine function lies in the symmetry plane of the transition region 9.

Figures 14, 15, 16:
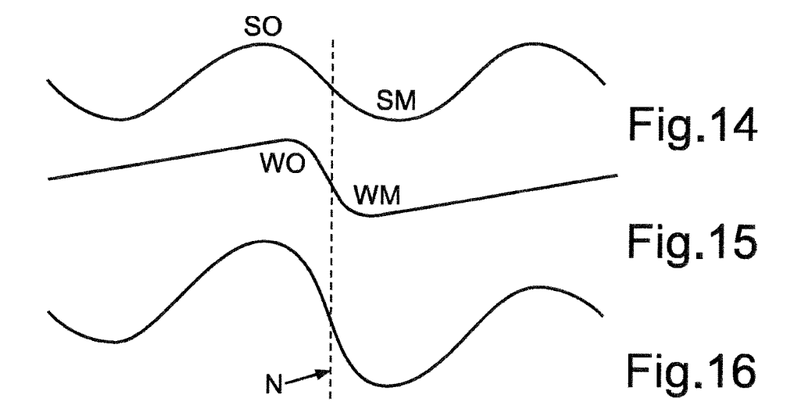
FIGS. 14 to 16 are curve representations of the surfaces according to FIGS. 11 to 13.

In FIGS. 14 to 16, the curve progressions of the surfaces according to FIGS. 11 to 13 are shown with the dashed symmetry plane.

Figure 17:
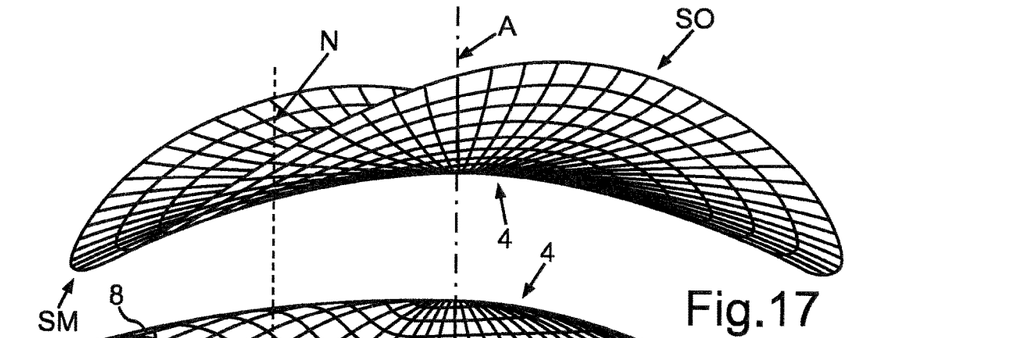
FIG. 17 is a perspective representation of a further surface showing the astigmatic summand portion in the function describing the overall surface.

In FIG. 17, a perspective view of further surface is shown, which is generated by the summand $a_2*r^2*\sin(2*\varphi)$ for the astigmatism, however, in comparison with FIG. 11 is positioned differently in comparison with the view shown in FIG. 11 in the circumferential direction about the axis A.

The surface is configured as saddle surface so that on the lens surface a toric shape is rendered.

Figure 18:
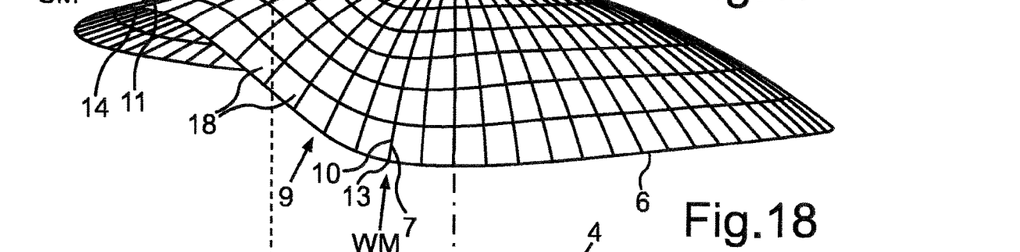
FIG. 18 is the view according to FIG. 2 in slightly rotated perspective in comparison with FIG. 2.

In FIG. 18, a view of the surface 4 according to FIG. 2 and FIG. 12 is shown, wherein in comparison with FIG. 2 slightly rotated view is shown.

Figure 19:
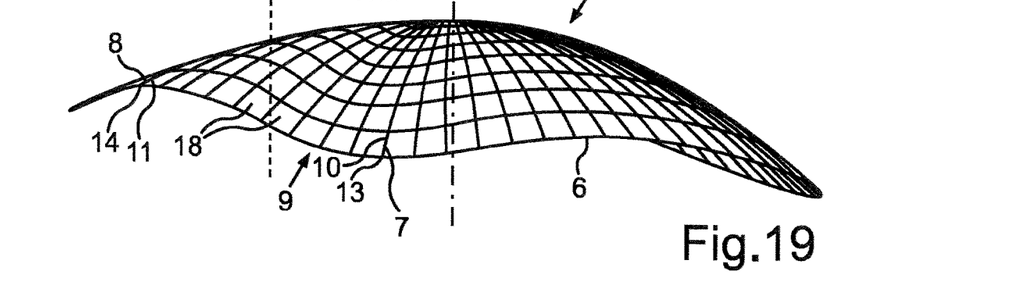
FIG. 19 is a perspective view of an embodiment of an optical surface of an optical part of an embodiment of an eye lens according to the invention, which is configured according to FIG. 12 and additionally the surface is configured in such a way that the lens serves for correction of an astigmatism; and, FIGS. 20 to 22 are curve representations of the surfaces according to FIGS. 17 to 19.

In FIG. 19, an embodiment of a lens configured for the correction of an astigmatism with represented surface 4 of the optical part is shown. In this connection the surface 4 in FIG. 18 is shown in comparable position to FIG. 17 so that the difference of the surface shape can be seen, between the lens with and without correction effect of an astigmatism.

In FIG. 19, the overlapping of the surfaces according to FIGS. 17 and 18 is shown. In this connection, it is envisaged in the embodiment that, for the surface according to FIG. 19, starting from the surface of FIG. 12, an additional saddle surface according to FIG. 17 is added so that an actual overall surface in FIG. 19 forms. Besides, the explanations given in the above apply.

Figure 20:
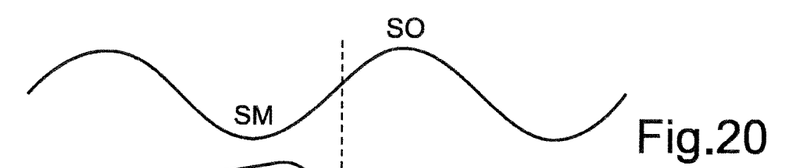
Figures 21, 22:
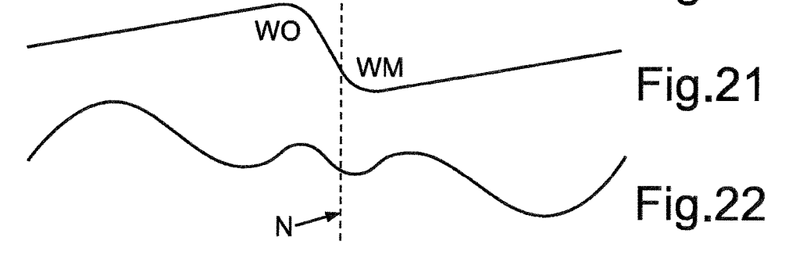

In FIGS. 20 to 22, the curve progressions of the surfaces according to FIGS. 17 to 19 with the dashed symmetry plane are represented.

The eye lens 1 is configured in particular as depth of focus lens. It is configured as refractive lens. This is realized in particular to the effect that in the radial direction from the axis A to the circumference 6 no periodic wave or valley profile is realized.

It is understood that the foregoing description is that of the preferred embodiments of the invention and that various changes and modifications may be made thereto without departing from the spirit and scope of the invention as defined in the appended claims.

What is claimed is:

1. An eye lens comprising:
a lens body defining a principal axis (A) and having a first optical surface;
said first optical surface being at least partly configured to have a structure having a turn with a pitch extending about said principal axis (A) from a beginning to an end;
a transition region formed between said beginning and said end of said turn;
said transition region passing into said turn with a beginning edge and an end edge;
said beginning edge extending between said principal axis (A) and a first peripheral location and said end edge extending between said principal axis (A) and a second peripheral location;
said beginning edge being projected into a plane (H) perpendicular to said principal axis (A);
said end edge being projected into said plane (H) perpendicular to said principal axis (A); and,
wherein at least one of the following applies: said beginning edge exhibits a non-linear course; and, said end edge exhibits a non-linear course.

2. The eye lens of claim 1, wherein at least one of the following applies:
said beginning edge is curved over the entire length thereof; and,
said end edge is curved over the entire length thereof.

3. The eye lens of claim 1, wherein at least one of the following applies:
said beginning edge has a non-linear course, which, in comparison to a linear connection between said principal axis (A) and said first peripheral location viewed in a peripheral direction about said principal axis (A), is configured to extend in a direction toward said end edge; and,
said end edge has a non-linear course, which, in comparison to a linear connection between said principal axis (A) and said second peripheral location viewed in the peripheral direction about said principal axis (A), is configured to extend in a direction toward said beginning edge.

4. The eye lens of claim 1, wherein said transition region defines a surface which is formed so that at least at said beginning edge between said principal axis (A) and said first peripheral location, a course is configured for which a slope of said surface of said transition region, when viewed in the peripheral direction, has the same slope course at all radial locations of said beginning edge.

5. The eye lens of claim 4, wherein said transition region defines a surface which is formed so that at least at said beginning edge, over the entire length thereof, between said principal axis (A) and said first peripheral location, a course is configured for which a slope of said surface of said transition region, when viewed in the peripheral direction, has the same slope course at all radial locations of said beginning edge.

6. The eye lens of claim 4, wherein said transition region defines a surface which is formed so that at least at said end edge between said principal axis (A) and said second peripheral location, a course is configured for which a slope of said surface of said transition region, when viewed in the peripheral direction, has the same slope course at all radial locations of said end edge.

7. The eye lens of claim 6, wherein said transition region defines a surface which is formed so that at least at said end edge, over the entire length thereof, between said principal axis (A) and said second peripheral location, a course is configured for which a slope of said surface of said transition region, when viewed in the peripheral direction, has the same slope course at all radial locations of said end edge.

8. The eye lens of claim 1, wherein said transition region defines a surface, when viewed in a section at a radial distance to said principal axis (A) and through said transition region, is configured to have a contour course which is at least partly configured to be nonlinear.

9. The eye lens of claim 8, wherein said contour course is at least partly configured to be a parabola.

10. The eye lens of claim 8, wherein said contour course is at least partly defined by a cubic function or is at least partly defined by a circular path section.

11. The eye lens of claim 8, wherein said contour course, between said beginning edge and said end edge, is symmetrical to a symmetry plane disposed, in a peripheral direction about said principal axis (A), at the same angle distance from each of said beginning edge and said end edge.

12. The eye lens of claim 11, wherein at least one of the following applies:
the slope course between said beginning edge and the symmetry plane is the same at all radial locations; and,
the slope course between said end edge and the symmetry plane is the same at all radial locations.

13. The eye lens of claim 4, wherein at least one of the following applies:

the slope course between said beginning edge and the symmetry plane is the same at all radial locations, wherein the symmetry plane is disposed, in a peripheral direction about said principal axis (A), at the same angle distance from each of said beginning edge and said end edge; and, the slope course between said end edge and the symmetry plane is the same at all radial locations.

14. The eye lens of claim 6, wherein at least one of the following applies:
the slope course between said beginning edge and a symmetry plane is the same at all radial locations, wherein the symmetry plane is disposed, in a peripheral direction about said principal axis (A), at the same angle distance from each of said beginning edge and said end edge; and,
the slope course between said end edge and the symmetry plane is the same at all radial locations.

15. The eye lens of claim 1, wherein a surface portion of said transition region is projected into the plane (H) disposed perpendicular to said principal axis (A) and is delimited by the projected beginning edge and the projected end edge; and, said surface portion of said transition region is smaller than a surface in said plane (H) delimited by two linear surface edges of which one extends from the principal axis (A) through said first peripheral location and the other extends from said principal axis (A) through said second peripheral location.

16. The eye lens of claim 1, wherein said first optical surface has an asphericity which varies about said principal axis (A).

17. The eye lens of claim 1, wherein said first optical surface has an asphericity which varies about said principal axis (A) and increases continuously.

18. The eye lens of claim 1, wherein said first optical surface of said lens body is so configured that the refractive power of said lens body in a peripheral direction about said principal axis (A) for a rotation in a range between 1 diopter and 5 diopters changes.

19. The eye lens of claim 18, wherein said refractive power changes continuously.

20. The eye lens of claim 18, wherein said range is between 1 diopter and 4 diopters.

21. The eye lens of claim 1, wherein the refractive power of said lens body outside of said transition region changes linearly as a function of the angle in the peripheral direction about said principal axis (A).

22. The eye lens of claim 1, wherein said transition region has an angle width of less than 7° in the peripheral direction about said principal axis (A).

23. The eye lens of claim 22, wherein said transition region is measured between said first and second peripheral locations.

24. The eye lens of claim 22, wherein said angle width lies between 3° and 6.5°.

25. The eye lens of claim 1, wherein said first optical surface is so configured that as a visual defect, an astigmatism is correctable.

26. The eye lens of claim 1, wherein a rear second optical surface of said optical body is configured to be symmetrical to said first optical surface with reference to a plane (H) disposed perpendicularly to said principal axis (A).

27. The eye lens of claim 1, wherein said eye lens is a depth of field lens.

* * * * *

UNITED STATES PATENT AND TRADEMARK OFFICE
CERTIFICATE OF CORRECTION

PATENT NO. : 10,098,726 B2
APPLICATION NO. : 15/045129
DATED : October 16, 2018
INVENTOR(S) : Gerlach et al.

Page 1 of 1

It is certified that error appears in the above-identified patent and that said Letters Patent is hereby corrected as shown below:

In the Specification

<u>In Column 15:</u>
Line 13: insert -- a -- before "slightly rotated view is shown.".

In the Claims

<u>In Column 17:</u>
Line 1: Claim 13 delete "beginning edge and the" and substitute -- beginning edge and a -- therefor.

Signed and Sealed this
Twenty-sixth Day of March, 2019

Andrei Iancu
*Director of the United States Patent and Trademark Office*